(12) United States Patent
Yasui et al.

(10) Patent No.: US 10,184,905 B2
(45) Date of Patent: Jan. 22, 2019

(54) RADIATION DETECTION APPARATUS AND RADIATION DETECTOR

(71) Applicant: HORIBA, Ltd., Kyoto-shi, Kyoto (JP)

(72) Inventors: Kengo Yasui, Kyoto (JP); Daisuke Matsunaga, Kyoto (JP)

(73) Assignee: HORIBA, LTD., Kyoto (JP)

( * ) Notice: Subject to any disclaimer, the term of this patent is extended or adjusted under 35 U.S.C. 154(b) by 240 days.

(21) Appl. No.: 15/133,753

(22) Filed: Apr. 20, 2016

(65) Prior Publication Data

US 2016/0313265 A1 Oct. 27, 2016

(30) Foreign Application Priority Data

Apr. 23, 2015 (JP) ................................. 2015-088549

(51) Int. Cl.
*G01N 23/00* (2006.01)
*G01N 23/223* (2006.01)
(52) U.S. Cl.
CPC .................. *G01N 23/223* (2013.01)
(58) Field of Classification Search
CPC .................................................. G01N 23/223
See application file for complete search history.

(56) References Cited

U.S. PATENT DOCUMENTS

| 2007/0114429 A1 | 5/2007 | Bhadare |
| 2012/0288058 A1 | 11/2012 | Maeyama et al. |
| 2016/0116424 A1* | 4/2016 | Furukawa ............ G01N 23/223 378/44 |

FOREIGN PATENT DOCUMENTS

| JP | 2007147595 A | 6/2007 |
| JP | 2008304372 A | 12/2008 |

OTHER PUBLICATIONS

Japanese Offie Action issued by the Japanese Patent Office in relation to Japanese Application No. 2015-088549 dated Oct. 30, 2018 (3 pages) along with English language translation (3 pages).

* cited by examiner

*Primary Examiner* — Dani Fox
(74) *Attorney, Agent, or Firm* — Robert P. Michal, Esq.; Carter, DeLuca, Farrell & Schmidt, LLP

(57) ABSTRACT

Three or more tubular radiation detectors are arranged around an irradiation axis of radiation directed to a sample from an irradiation unit such that the end face thereof is opposed to the position irradiated with radiation. The radiation emitted from the sample enters the radiation detector through an end face and is detected. In the radiation detector, the length in the direction parallel to the straight line which is on the plane orthogonal to the irradiation axis and is perpendicular to the central axis continuously decreases from a position along the central axis to the end face. The size of each radiation detector around the irradiation axis is reduced as it approaches the end face, preventing the radiation detectors from interfering with one another and allowing the radiation detector to be closer to the sample compared to the conventional case. This makes it possible for the radiation detection apparatus to detect radiation from the sample with high efficiency.

4 Claims, 6 Drawing Sheets

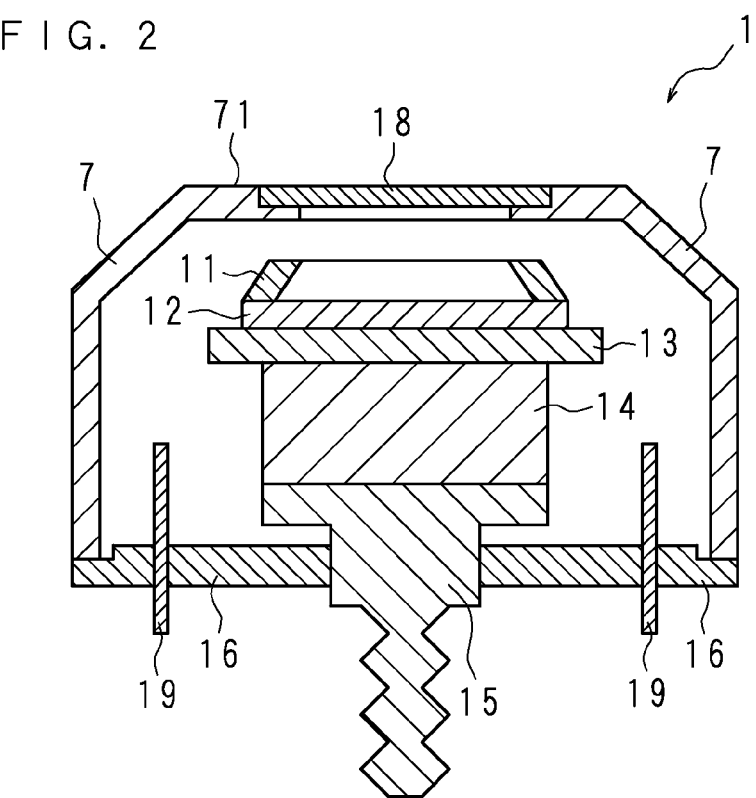
F I G. 2

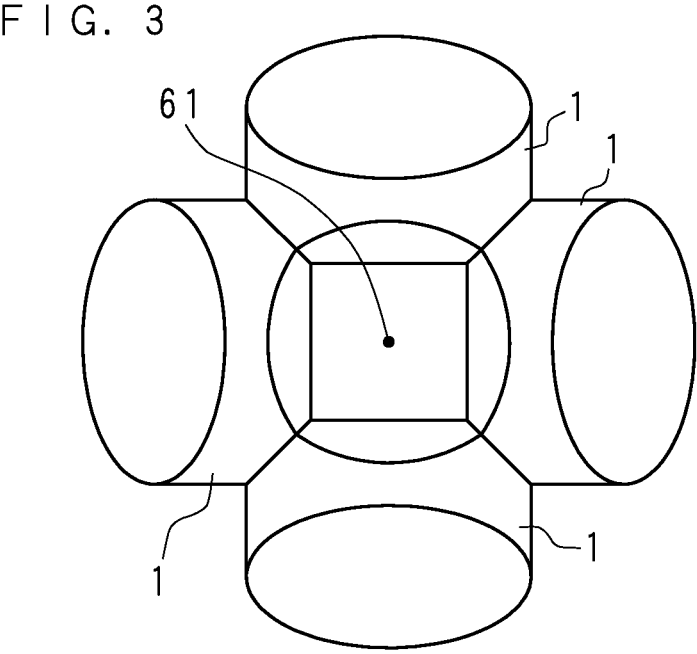
F I G. 3

F I G. 4
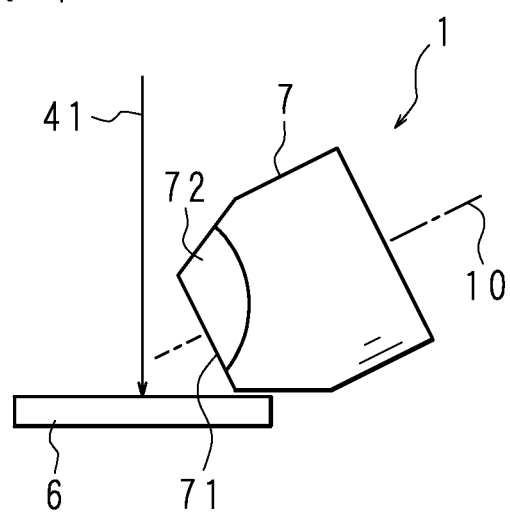

RADIATION DETECTION APPARATUS AND RADIATION DETECTOR

CROSS-REFERENCE TO RELATED APPLICATIONS

This Nonprovisional application claims priority under 35 U.S.C. § 119(a) on Patent Application No. 2015-088549 filed in Japan on Apr. 23, 2015, the entire contents of which are hereby incorporated by reference.

BACKGROUND

1. Technical Field

The present invention relates to a radiation detection apparatus employing multiple radiation detectors and to a radiation detector.

2. Description of Related Art

An example radiation detector for detecting radiation such as X-ray detects radiation with the use of a radiation detecting element made of a semiconductor. The radiation detecting element is disposed in a tightly-sealed tubular housing, and a radiation detector is formed in a columnar shape as a whole. The radiation detector having such a configuration is described in Japanese Patent Application Laid-Open No. 2007-147595.

An example radiation detection apparatus employing a radiation detector irradiates a sample with radiation such as electron beam, X-ray or the like and detects radiation emitted from the sample irradiated with the radiation with the use of the radiation detector.

Such a radiation detection apparatus includes, for example, an X-ray fluorescence spectrometer. A radiation detection apparatus for detecting radiation with the use of multiple radiation detectors has been developed in order to detect radiation emitted from a sample with high efficiency.

SUMMARY OF THE INVENTION

In order to further enhance the efficiency of a radiation detection apparatus for detecting radiation from a sample, a radiation detector may be located closer to the sample. In the case of a radiation detection apparatus with multiple radiation detectors, however, the radiation detectors interfere with one another if located too close to a sample. Thus, there is a limit in enhancement of efficiency for detecting radiation by placing a radiation detector closer to a sample.

The present invention has been made in view of the circumstances described above, and aims to provide a radiation detection apparatus and a radiation detector that allow a radiation detector to be located closer to a sample than in the conventional case to enhance the efficiency for detecting radiation.

A radiation detection apparatus according to the present invention comprises, an irradiation unit irradiating a sample with radiation, and a columnar radiation detector detecting radiation emitted from the sample. Three or more of the radiation detectors are arranged around an irradiation axis of radiation directed to the sample by the irradiation unit such that one end face of each of the radiation detectors is opposed to a position irradiated with radiation on the sample, and a central axis of each of the radiation detectors non-perpendicularly intersects with a plane orthogonal to the irradiation axis. Each of the radiation detectors has a length in a direction parallel to a straight line which is on the plane and is perpendicular to the central axis, the length continuously decreasing from a predetermined position toward the one end face along the central axis. At a portion of each of the radiation detectors where the length decreases along the central axis, a length of a part of the radiation detector in the direction within a plane orthogonal to the central axis is longer as the part is closer to the sample.

In the radiation detection apparatus according to the present invention, each of the radiation detectors has a planar portion at a circumferential surface which is proximate to another radiation detector.

A radiation detection apparatus according to the present invention comprises a columnar radiation detector for detecting radiation emitted from a sample. Three or more of the radiation detectors are arranged around a predetermined axis such that one end face of each of the radiation detectors is opposed to the sample, and a central axis of each of the radiation detectors non-perpendicularly intersects with a plane orthogonal to the predetermined axis. Each of the radiation detectors has a length in a direction parallel to a straight line which is on the plane and is perpendicular to the central axis, the length continuously decreasing from a predetermined position toward the one end face along the central axis. At a portion of each of the radiation detectors where the length decreases along the central axis, a length of a part of the radiation detector in the direction within a plane orthogonal to the central axis is longer as the part is closer to the sample.

A radiation detector of a columnar shape according to the present invention comprises a window which radiation passes through and is at one end of the radiation detector. A length in a first direction parallel to a predetermined straight line perpendicular to a central axis continuously decreases from a predetermined position toward the one end along the central axis. At a portion where the length decreases along the central axis, a length of a part in the first direction within a plane orthogonal to the central axis monotonously changes along a second direction orthogonal to the first direction.

According to the present invention, the radiation detection apparatus includes three or more columnar radiation detectors around an irradiation axis of radiation to be directed to a sample, each of the radiation detectors having one end face opposed to the position irradiated with radiation. The plane orthogonal to the irradiation axis non-perpendicularly intersects with the central axis of the radiation detector. In the radiation detector, the length in a direction parallel with a straight line which is on the plane orthogonal to the irradiation axis and is perpendicular to the central axis of the radiation detector is continuously decreased from a position along the central axis toward the end face. The length of each radiation detector around the irradiation axis decreases toward the end face thereof, which prevents the radiation detectors from interfering with one another, allowing the radiation detectors to be located closer to a sample than in the conventional case. Furthermore, in the plane orthogonal to the central axis at a portion where the length of the radiation detector in the said direction continuously decreases along the central axis, a length of a part of the radiation detector in the said direction is longer as the part of the radiation detector is closer to the sample. Parts of multiple radiation detectors, which easily interfere with one another in a situation that the multiple radiation detectors are arranged around the irradiation axis, are made shorter, while other parts thereof that do not easily interfere with one another in the situation are made longer. This allows the area of the radiation detector that is orthogonal to the central axis to be as large as possible while the radiation detector is located closer to a sample.

Furthermore, in the present invention, a portion of the circumferential surface of the radiation detector that is proximate to another radiation detector is made in a planar shape. Compared to the case where the portion proximate to another radiation detector is made in a curved shape, the area of the radiation detector orthogonal to the central axis may be increased without changing the distance between radiation detectors.

According to the present invention, multiple radiation detectors may be located closer to a sample than in the conventional case, so that radiation from the sample may be detected with high efficiency. Therefore, the radiation detection apparatus produces a beneficial effect such as highly sensitive detection of radiation.

The above and further objects and features of the invention will more fully be apparent from the following detailed description with accompanying drawings.

BRIEF DESCRIPTION OF SEVERAL VIEWS OF THE DRAWINGS

FIG. 2 is a schematic section view of a radiation detector;

FIG. 3 is a schematic plan view illustrating an arrangement example of multiple radiation detectors;

FIG. 4 is a schematic side view of one radiation detector;

DETAILED DESCRIPTION

The present invention will specifically be described below with reference to the drawings illustrating the embodiment thereof.

Figure 1:
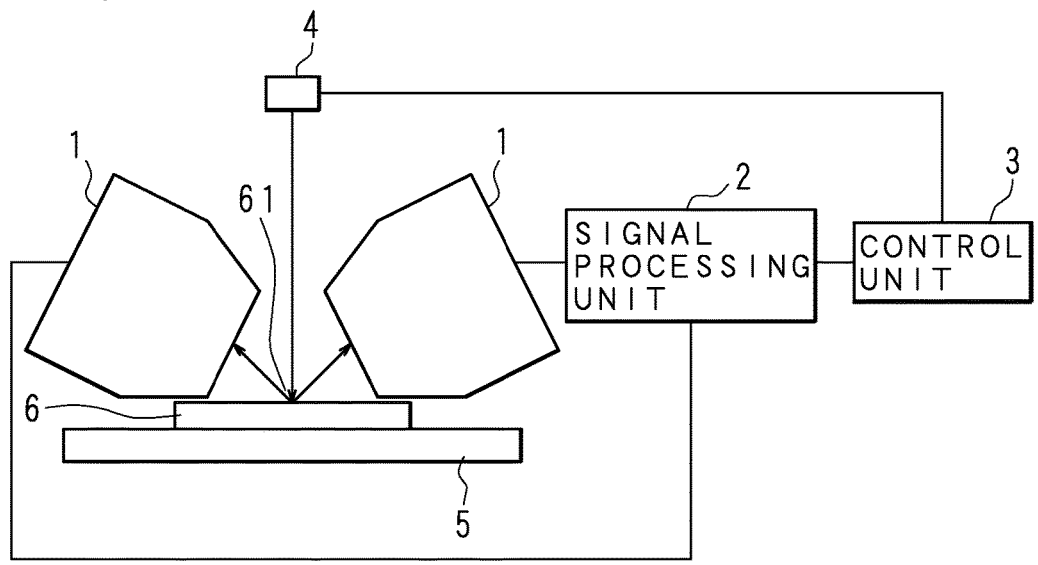
FIG. 1 is a block diagram illustrating the configuration of a radiation detection apparatus.

FIG. 1 is a block diagram illustrating the configuration of a radiation detection apparatus. The radiation detection apparatus is, for example, an X-ray fluorescence spectrometer. The radiation detection apparatus includes an irradiation unit 4 irradiating a sample 6 with radiation such as electron beam or X-ray, a sample table 5 on which the sample 6 having the shape of a flat plate is held, and multiple radiation detectors 1. While two radiation detectors 1 are illustrated in FIG. 1, the radiation detection apparatus includes three or more radiation detectors 1. The irradiation unit 4 irradiates the sample 6 with radiation, which generates radiation such as X-ray fluorescence at the sample 6, and the radiation detector 1 detects the radiation emitted from the sample 6. In FIG. 1, the radiation is indicated by arrows. The position irradiated with radiation on the sample 6 is indicated by the numeral 61. The radiation detector 1 outputs a signal proportional to the energy of the detected radiation. The radiation detector 1 is connected to a signal processing unit 2 for processing a signal output from the radiation detector 1. The signal processing unit 2 counts signals of different values output from the radiation detector 1, to generate a relationship between the energy of radiation and the counted number, i.e. the spectrum of radiation. The signal processing unit 2 may generate a spectrum by adding the results of detection at the multiple radiation detectors 1, or a spectrum by averaging the results of detection at the multiple radiation detectors 1. The signal processing unit 2 and the irradiation unit 4 are connected to the control unit 3 for controlling the entire radiation detection apparatus. The control unit 3 controls the operations of the signal processing unit 2 and the irradiation unit 4.

FIG. 2 is a schematic section view of the radiation detector 1. The radiation detector 1 includes a plate-like base 16. A cap-shaped cover 7 is placed over one surface side of the base 16. The cover 7 has a shape formed by connecting a truncated cone to one end of a cylinder, the other end of the cylinder being joined to the base 16. As the cover 7 is connected to the base 16, the radiation detector 1 is formed in a columnar shape as a whole. The base 16 and the cover 7 are made of metal such as iron and are welded. A window 18 of a flat plate shape made of a material such as beryllium which allows radiation to pass therethrough is formed at an end face 71 at the top end of the cover 7. Inside the cover 7 is tightly sealed, and is depressurized or filled with inert gas.

Inside the cover 7, a tubular collimator 11, a radiation detecting element 12 made of a semiconductor, a wiring board 13 and a Peltier device 14 are disposed. The radiation detecting element 12 is, for example, a silicon drift detector (SDD). The radiation detecting element 12 of a plate-like shape is mounted on the surface of the wiring board 13 and is disposed at the position opposed to the window 18. The collimator 11 is formed in a tubular shape with both ends thereof opened, with a material which shields against radiation, and is disposed between the radiation detecting element 12 and the window 18. One end of the collimator 11 is opposed to the window 18, while the other end thereof is in contact with the surface of the radiation detecting element 12. The collimator 11 shields against a part of radiation which passed through the window 18, and the radiation detecting element 12 detects radiation which remains without being shielded against by the collimator 11. A portion inside the collimator 11 on the surface of the radiation detecting element 12 which is opposed to the window 18 is an incident surface for radiation to be detected.

A heat absorbing part of the Peltier device 14 is in thermal contact with the rear surface of the wiring board 13. The heat releasing part of the Peltier device 14 is opposed to the inner surface of the base 16. Moreover, the radiation detector 1 includes a cold finger 15 which is in thermal contact with the heat releasing part of the Peltier device 14. The cold finger 15 is made of a material with high thermal conductivity. The cold finger 15 is configured to include a plate-like part which is in thermal contact with the heat releasing part of the Peltier device 14 and a bolt-like part protruding from the plate-like part toward the base 16. The bolt-like part of the cold finger 15 penetrates the base 16 and protrudes from the outer surface of the base 16. The wiring board 13 and the Peltier device 14, and the Peltier device 14 and the cold finger 15 may be in direct contact with each other or a heat conducting material may be interposed in between. The bolt-like part of the cold finger 15 protruding from the outer surface of the base 16 is connected to the heat releasing unit located outside the radiation detector 1. The heat releasing unit is a heat sink, for example. The radiation detecting element 12 is cooled by the Peltier device 14 through the wiring substrate 13, and the heat from the radiation detecting element 12 is conducted from the Peltier device 14 to the cold finger 15, and is released from the heat releasing unit. Furthermore, multiple lead pins 19 for supplying power and input/output of signals penetrate the base 16.

FIG. 3 is a schematic plan view illustrating an example of arrangement of multiple radiation detectors 1. FIG. 3 illustrates an example where the radiation detection apparatus is provided with four radiation detectors 1. The irradiation axis of radiation directed to the sample 6 by the irradiation unit 4 is orthogonal to the sheet of FIG. 3. Each of the radiation detectors 1 has a columnar shape as a whole, with a window 18 formed at one end thereof. In FIG. 3, the cold finger 15 and lead pins 19 included in the radiation detector 1 are not illustrated. Multiple radiation detectors 1 are arranged around the irradiation axis of the radiation emitted by the irradiation unit 4. Each of the radiation detectors 1 is arranged such that the central axis of the radiation detector 1 non-perpendicularly crosses the plane orthogonal to the irradiation axis of radiation, and is arranged such that the window 18 faces the position 61 on the sample 6 that is irradiated with radiation. The radiation emitted from the sample 6 being irradiated with radiation is directed in different directions. By the multiple radiation detectors 1 being placed around the irradiation axis, the emitted radiation may enter any one of the radiation detectors 1 with high possibility, so that radiation may be detected by the radiation detection apparatus with high possibility. While the radiation detector 1 includes a portion having a tapered shape as will described later, the central axis passes through the center or the center of gravity of a cross section of a not-tapered portion of the radiation detector 1. The central axis of the radiation detector 1 is preferably orthogonal to the incident surface of the radiation detecting element 12, and may pass through the center or center of gravity of the incident surface of the radiation detecting element 12. It is to be noted that the number of the radiation detectors 1 included in the radiation detection apparatus may also be three, five or more.

Figure 5:
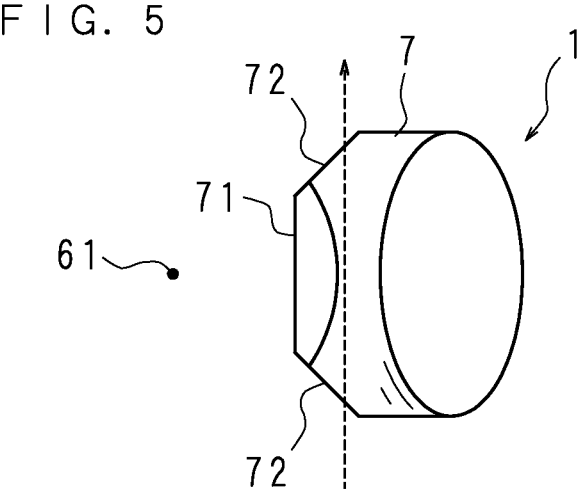
FIG. 5 is a schematic plan view of one radiation detector.
Figure 6:
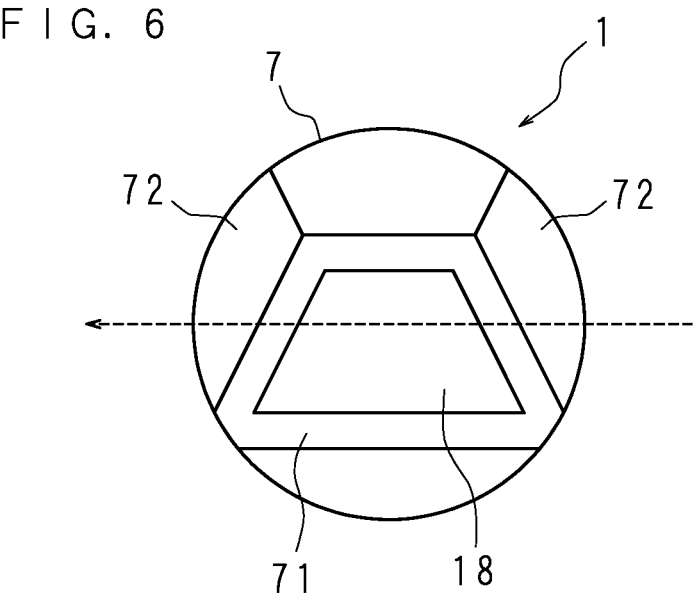
FIG. 6 is a schematic front view of a radiation detector with an end face being the front.

FIG. 4 is a schematic side view of one radiation detector 1. FIG. 5 is a schematic plan view of one radiation detector 1. FIG. 6 is a schematic front view of the radiation detector 1 with an end face 71 being the front. In FIG. 4 and FIG. 5, the cold finger 15 and lead pins 19 are not illustrated. In FIG. 4, the irradiation axis 41 of radiation directed to the sample 6 by the irradiation unit 4 is indicated by a solid arrow, and the central axis 10 of the radiation detector 1 is indicated by a dashed-dotted line. The central axis 10 is orthogonal to the sheet of FIG. 6. Furthermore, in FIGS. 5 and 6, a direction parallel to the straight line which is on the plane orthogonal to the central axis 10 and is perpendicular to the irradiation axis 41 is indicated by a dotted arrow. Assuming that the direction along the irradiation axis 41 is a vertical direction, the direction indicated by the dotted arrow corresponds to a lateral direction. The lateral direction orthogonal to the central axis 10 is a direction orthogonal to the sheet of FIG. 4. As illustrated in FIG. 5, the length of the cover 7 in the lateral direction is continuously decreased from a predetermined position toward the end face 71 along the central axis 10. Since the size of the cover 7 around the irradiation axis 41 is smaller as it approaches the end face 71, the covers 7 of the multiple radiation detectors 1 do not easily interfere with one another if the radiation detectors 1 are disposed around the irradiation axis 41 as illustrated in FIG. 3. It is therefore possible to arrange the multiple radiation detectors 1 with their end faces 71 located closer to the sample 6 compared to the conventional case.

The circumferential surface of a portion of the cover 7 where the length of the cover 7 in the lateral direction is decreased continuously along the central axis 10 forms a proximate portion 72 which is proximate to other radiation detectors 1. The proximate portion 72 has a planar shape. As illustrated in FIGS. 5 and 6, the radiation detector 1 has two proximate portions 72 so that other radiation detectors 1 may be located proximate to both sides of one radiation detector 1. The two proximate portions 72 are not in parallel with each other but are inclined at 5° or more, preferably 10° or more, with respect to each other in the plane orthogonal to the central axis 10. Each of the proximate portions 72 has a planar shape, which can increase the area of the radiation detector 1 orthogonal to the central axis 10 without changing the distance between the radiation detectors 1, compared to the case where the proximate portion 72 has a curved shape.

In FIG. 6, the lower part of the radiation detector 1 is the part closer to the sample 6. At the end face 71 of the cover 7, the length of the cover 7 in the lateral direction is longer as it approaches the sample 6. Likewise, at the portion where the length of the cover 7 in the lateral direction is decreased continuously along the central axis 10, the length of the cover 7 in the lateral direction in the plane orthogonal to the central axis 10 is longer as it approaches the sample 6 in the plane. The two proximate portions 72 are inclined with respect to the straight line which is on the plane orthogonal to the irradiation axis 41 and is perpendicular to the central axis 10 such that the distance between the proximate portions 72 is longer as they approach the sample 6. Thus, the distance between the proximate portions 72 is longer when closer to the sample 6. When the surface of the window 18 is divided by the plane which passes the intersection between the surface of the window 18 and the central axis 10 and is orthogonal to the irradiation axis 41, the surface area at a portion near the sample 6 is larger than the surface area at a portion distant from the sample 6. The surface of the window 18 preferably has a trapezoidal shape. As illustrated in FIG. 3, in the state where the radiation detectors 1 are arranged around the irradiation axis 41 such that their end faces 71 being opposed to the irradiated position 61 and that the central axis 10 non-perpendicularly crosses the plane orthogonal to the irradiation axis 41, the radiation detectors 1 easily interfere with one another at a portion comparatively distant from the sample 6. The length of each radiation detector 1 in the lateral direction is made shorter at the portion distant from the sample 6 where the radiation detectors 1 easily interfere with one another, while it is made longer at a portion near the sample 6 where they do not easily interfere with one another. As such, in the state where the end face 71 is closer to the sample 6, the area of the end face 71 as well as the area of the radiation detector 1 orthogonal to the central axis 10 may be increased as much as possible. The increase in the area of the end face 71 allows the window 18 to also have a large area, increasing the radiation entering the radiation detector 1. The increase in the area of the radiation detector 1 orthogonal to the central axis 10 allows the radiation detecting element 12 disposed in the cover 7 to also have a large area, enhancing the efficiency of detecting radiation. In order to enhance the efficiency of detecting radiation, the portions of the collimator 1 and the radiation detecting element 12 that are opposed to the window 18 may preferably have a shape contouring the inner surface of the cover 17.

As has been described in detail, the radiation detection apparatus includes multiple radiation detectors 1 arranged around the irradiation axis 41 of radiation directed to the sample 6, the size of each radiation detector 1 around the irradiation axis 41 being reduced as it approaches the end face 71. The covers 7 of the radiation detectors 1 do not easily interfere with one another, allowing the radiation detectors 1 to be closer to the sample 6 compared to the conventional case. This increases the percentage of radiation emitted from the sample 6 entering any one of the radiation detectors 1, and also enhances the efficiency of detecting radiation at the radiation detection apparatus. Accordingly, the radiation detection apparatus can detect radiation with high sensitivity and can analyze the sample 6 with high accuracy.

Furthermore, in the present embodiment, the proximate portion 72 at the circumferential surface of one radiation detector 1 that is proximate to another radiation detector 1 is formed in a planar shape. Moreover, in the plane orthogonal to the central axis 10 near the end face 71 of the radiation detector 1, the length of a part of the radiation detector 1 in the lateral direction, when the direction parallel to the irradiation axis 41 is the vertical direction, is longer as the part is closer to the sample 6. This ensures the window 18 through which the radiation enters to have an area as large as possible and ensures the radiation detector 1 to have an area orthogonal to the central axis 10 as large as possible, even when the radiation detector 1 is located closer to the sample 6. Accordingly, the efficiency of detecting radiation at the radiation detector 1 is more increased, allowing the radiation detection apparatus to detect radiation with high sensitivity.

While an example where multiple radiation detectors 1 are arranged around the irradiation axis 41 is described in the present embodiment, the radiation detection apparatus may also take a form in which multiple radiation detectors 1 are arranged around a predetermined axis other than the irradiation axis 41. For example, the radiation detection apparatus may have a form in which the radiation detectors 1 are arranged around a predetermined axis, and the radiation is directed to the sample 6 in a direction inclined with respect to the predetermined axis or the radiation passes between any of the radiation detectors 1 and the sample table 5 before being directed to the sample 6. Moreover, the radiation detection apparatus may also take a form of directing radiation to the rear side of the sample 6.

It is noted that, as used herein and in the appended claims, the singular forms "a", "an", and "the" include plural referents unless the context clearly dictates otherwise.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A radiation detection apparatus, comprising:
an irradiation unit irradiating a sample with radiation; and
a columnar radiation detector detecting radiation emitted from the sample, wherein
three or more of the radiation detectors are arranged around an irradiation axis of radiation directed to the sample by the irradiation unit such that one end face of each of the radiation detectors is opposed to a position irradiated with radiation on the sample, and a central axis of each of the radiation detectors non-perpendicularly intersects with a plane orthogonal to the irradiation axis,
each of the radiation detectors has a length in a direction parallel to a straight line which is on the plane and is perpendicular to the central axis, the length continuously decreasing from a predetermined position toward the one end face along the central axis, and
at a portion of each of the radiation detectors where the length decreases along the central axis, a length of a part of the radiation detector in the direction within a plane orthogonal to the central axis is longer as the part is closer to the sample.

2. The radiation detection apparatus according to claim 1, wherein
each of the radiation detectors has a planar portion at a circumferential surface which is proximate to another radiation detector.

3. A radiation detection apparatus, comprising
a columnar radiation detector for detecting radiation emitted from a sample, wherein
three or more of the radiation detectors are arranged around a predetermined axis such that one end face of each of the radiation detectors is opposed to the sample, and a central axis of each of the radiation detectors non-perpendicularly intersects with a plane orthogonal to the predetermined axis,
each of the radiation detectors has a length in a direction parallel to a straight line which is on the plane and is perpendicular to the central axis, the length continuously decreasing from a predetermined position toward the one end face along the central axis, and
at a portion of each of the radiation detectors where the length decreases along the central axis, a length of a part of the radiation detector in the direction within a plane orthogonal to the central axis is longer as the part is closer to the sample.

4. A radiation detector of a columnar shape, comprising
a window which radiation passes through and is at one end of the radiation detector, wherein
a length in a first direction parallel to a predetermined straight line perpendicular to a central axis continuously decreases from a predetermined position toward the one end along the central axis,
at a portion where the length decreases along the central axis, a length of the portion in the first direction within a plane orthogonal to the central axis monotonously increases from a first side to a second side along a second direction orthogonal to the first direction, and
the portion includes, in a plane orthogonal to the central axis, a part having a length in the first direction being longer than a length of the portion along a straight line which is perpendicular to the central axis and parallel to the first direction.

* * * * *